(12) United States Patent
Knapp et al.

(10) Patent No.: US 7,398,118 B2
(45) Date of Patent: Jul. 8, 2008

(54) CUSTOMIZED MATERIAL FOR IMPROVED RADIOPACITY

(75) Inventors: David Knapp, Saint Paul, MN (US); Brian T. Berg, Saint Paul, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 556 days.

(21) Appl. No.: 11/095,429

(22) Filed: Mar. 31, 2005

(65) Prior Publication Data
US 2005/0169842 A1 Aug. 4, 2005

Related U.S. Application Data

(63) Continuation of application No. 10/140,738, filed on May 7, 2002, now Pat. No. 6,904,310.

(51) Int. Cl.
*A61B 6/00* (2006.01)
*H05G 1/70* (2006.01)

(52) U.S. Cl. .................................. 600/431; 378/92

(58) Field of Classification Search .................. 600/431, 600/432, 433, 434, 435, 425; 424/1, 4; 378/92, 378/93, 94, 95, 96; 250/302
See application file for complete search history.

(56) References Cited

U.S. PATENT DOCUMENTS

| | | | | |
|---|---|---|---|---|
| 4,432,370 A | * | 2/1984 | Hughes et al. | 600/431 |
| 4,672,212 A | * | 6/1987 | Brahme | 250/505.1 |
| 4,890,310 A | * | 12/1989 | Umetani et al. | 378/82 |
| 4,945,552 A | * | 7/1990 | Ueda et al. | 378/98.11 |
| 5,361,761 A | * | 11/1994 | Van Lysel et al. | 600/407 |
| 5,594,771 A | * | 1/1997 | Kawai | 378/98.2 |
| 2002/0039401 A1 | | 4/2002 | Salb | |

FOREIGN PATENT DOCUMENTS

WO  WO 02/05863 A1  1/2002
WO  WO 02/078764 A1  10/2002

* cited by examiner

*Primary Examiner*—Daniel Robinson
(74) *Attorney, Agent, or Firm*—Fish & Richardson P.C.

(57) ABSTRACT

A method for obtaining diagnostic information about a region of a living being, the region having a medical device with a radiopaque portion disposed therein. An X-ray beam having a first energy level in excess of the K-absorption edge of the radiopaque portion of the medical device is directed at the region to obtain a first image information and radiographically locate the medical device within the living being and an X-ray beam having second energy level at or below the K-absorption edge is applied to the region to obtain a second image information.

4 Claims, 4 Drawing Sheets

200

200

& # x 2 0 ; 
CUSTOMIZED MATERIAL FOR IMPROVED RADIOPACITY

CROSS-REFERENCE TO RELATED APPLICATIONS

This application is a continuation application of and claims priority to U.S. application Ser. No. 10/140,738, filed May 7, 2002, now U.S. Pat. No. 6,904,310 the entire contents of which are hereby incorporated by reference.

BACKGROUND OF THE INVENTION

Stents are placed or implanted within a blood vessel for treating stenoses, strictures or aneurysms therein. They are implanted to reinforce collapsing, partially occluded, weakened, or dilated sections of a blood vessel. They have also been implanted in other bodily vessels including arteries, veins, biliary ducts, urethras, fallopian tubes, bronchial tubes, the trachea and the esophagus.

Stents are typically either self-expanding or mechanically expandable via the application of radially outward force from within the stent, as by inflation of a balloon. Hybrid stents, e.g., stents which are both self-expanding and mechanically expandable are also known.

Stents may be produced from a wide variety of materials. Typically, radiopaque materials are incorporated into stents to facilitate visualizing them as they are delivered to desired bodily locations. The radiopaque material may be provided in the form of a coating, in the form of one or more marker bands which are attached to the stent or may be incorporated into the basic structure of the stent as by blending a radiopaque metal with a structural metal. The entirety of the stent may be radiopaque or only desired portions of the stent may be radiopaque, for example, the proximal and distal ends of the stent. In the case of a bifurcated stent, it may be desirable for the region of sidebranch access to be radiopaque.

While rendering regions of a stent radiopaque facilitates imaging the stent during delivery, the radiopacity of the stent may hinder visualizing the contents of the stent subsequent to expansion of the stent. Visualizing flow of a bodily fluid through a stent may be necessary in cases where restenosis has occurred subsequent to implantation of the stent. The darkness of the radiopaque region of the stent obscures the contents of the stent from the fluoroscopic image.

There remains a need to provide novel methods of imaging stents which allow for viewing the stent under fluoroscopy but which also allow for visualizing the contents of the stent.

All U.S. patents, applications and all other published documents mentioned anywhere in this application are incorporated herein by reference in their entirety.

Without limiting the scope of the invention, a brief summary of the claimed embodiments of the invention is set forth below. Additional details of the summarized embodiments of the invention and/or additional embodiments of the invention maybe found in the Detailed Description of the Invention below.

A brief abstract of one or more embodiments of the invention is provided as well for the purposes of complying with 37 C.F.R. 1.72.

SUMMARY OF THE INVENTION

In one embodiment, the invention is directed to a method of obtaining diagnostic information about a region of a living being, the region having a medical device including a radiopaque portion disposed therein. The radiopaque portion of the medical device is characterized by a K-absorption edge. In accordance with the method, an X-ray beam having a first energy level in excess of the K-absorption edge of the radiopaque portion of the medical device is applied to the region to obtain a first image information and radiographically locate the medical device within the living being. An X-ray beam having a second energy level at or below the K-absorption edge is applied to the region to obtain a second image information. Desirably, the step involving radiographically locating the medical device precedes the step of obtaining the second image information using an X-ray beam having a second energy level at or below the K-absorption edge.

In another embodiment, the invention is directed to a method of implanting a medical device which is expandable in a living body and monitoring flow through the medical device. The method comprises the steps of delivering the medical device on a catheter to a desired location in a living body, locating the medical device by imaging the medical device with an X-ray beam having a first energy level in excess of the K-absorption edge of the radiopaque portion of the medical device, manipulating the catheter to expand the expandable medical device and visualizing flow of a bodily fluid comprising a contrast agent through the medical device by imaging the medical device with an X-ray beam having a second energy level at or below the K-absorption edge of the medical device.

In yet another embodiment of the invention, the invention is directed to a method for radiographic imaging of a region of a body having a medical device with a radiopaque portion therein where the radiopaque portion has a K-absorption edge. The method comprises the steps of:

a) generating a plurality of X-ray beams with predetermined different energy spectra, at least one of the plurality of X-ray beams having a mean energy in excess of the K-absorption edge, at least one of the plurality of X-ray beams having a mean energy no greater than the K-absorption edge, b) illuminating the region with each of the plurality of beams; and c) acquiring a radiographic image of the region during illumination by each of the plurality of beams.

In yet another embodiment, the invention is directed to a stent having a flowpath therethrough. At least a portion of the stent comprises an amount of a radiopaque material which is characterized by an attenuation curve having a K-absorption edge. The amount of radiopaque material is chosen such that when an X-ray beam having a mean energy in excess of the K-absorption edge energy is directed at the stent and a radiographic image acquired, the radiopaque material is visible in the image and radiographically obscures any fluid in the flowpath of the stent, and when an X-ray beam having a mean energy slightly below the K-absorption edge energy is directed at the stent, the radiopaque material is substantially transparent.

The invention is also directed to a method of designing a stent comprising the steps of selecting a stent structure, selecting a radiopaque material which is characterized by an attenuation curve having a K-absorption edge, selecting at least one portion of the stent structure which will be provided with the radiopaque material and calculating an amount of the radiopaque material which must be provided in the selected portion of the stent structure such that the selected portion of the stent structure will be radiographically visible when an X-ray beam having a mean energy in excess of the K-absorption edge energy is directed at the stent and such that the selected portion of the stent structure will be substantially radiographically transparent when an X-ray beam having a mean energy slightly below the K-absorption edge energy is directed at the stent.

The invention is further directed to a method of manufacturing a stent comprising the steps of selecting a stent structure, selecting a radiopaque material which is characterized by an attenuation curve having a K-absorption edge, selecting at least one portion of the stent structure which will be provided with the radiopaque material, calculating an amount of the radiopaque material which must be provided in the selected portion of the stent structure such that the selected portion of the stent structure will be radiographically visible when an X-ray beam having a mean energy in excess of the K-absorption edge energy is directed at the stent and such that the selected portion of the stent structure will be substantially radiographically transparent when an X-ray beam having a mean energy slightly below the K-absorption edge energy is directed at the stent, and constructing a stent having the selected stent structure and comprising the selected radiopaque material in the selected portion of the stent, the radiopaque material present in the calculated amount.

The invention is also directed to a method of monitoring a treatment of a selected bodily region. The method comprises the steps of delivering a therapeutic agent to a desired bodily region, the therapeutic agent comprising a radiopaque material characterized by a K-absorption edge, generating a plurality of X-ray beams with predetermined different energy spectra, at least one of the plurality of X-ray beams having a mean energy in excess of the K-absorption edge, at least one of the plurality of X-ray beams having a mean energy no greater than the K-absorption edge, illuminating the region with each of said plurality of beams and, acquiring a radiographic image of the region during illumination by each of said plurality of beams.

The invention is also directed to stents and other medical devices made in accordance with the inventive methods disclosed herein.

Additional details and/or embodiments of the invention are discussed below.

DETAILED DESCRIPTION OF THE INVENTION

Figure 1:
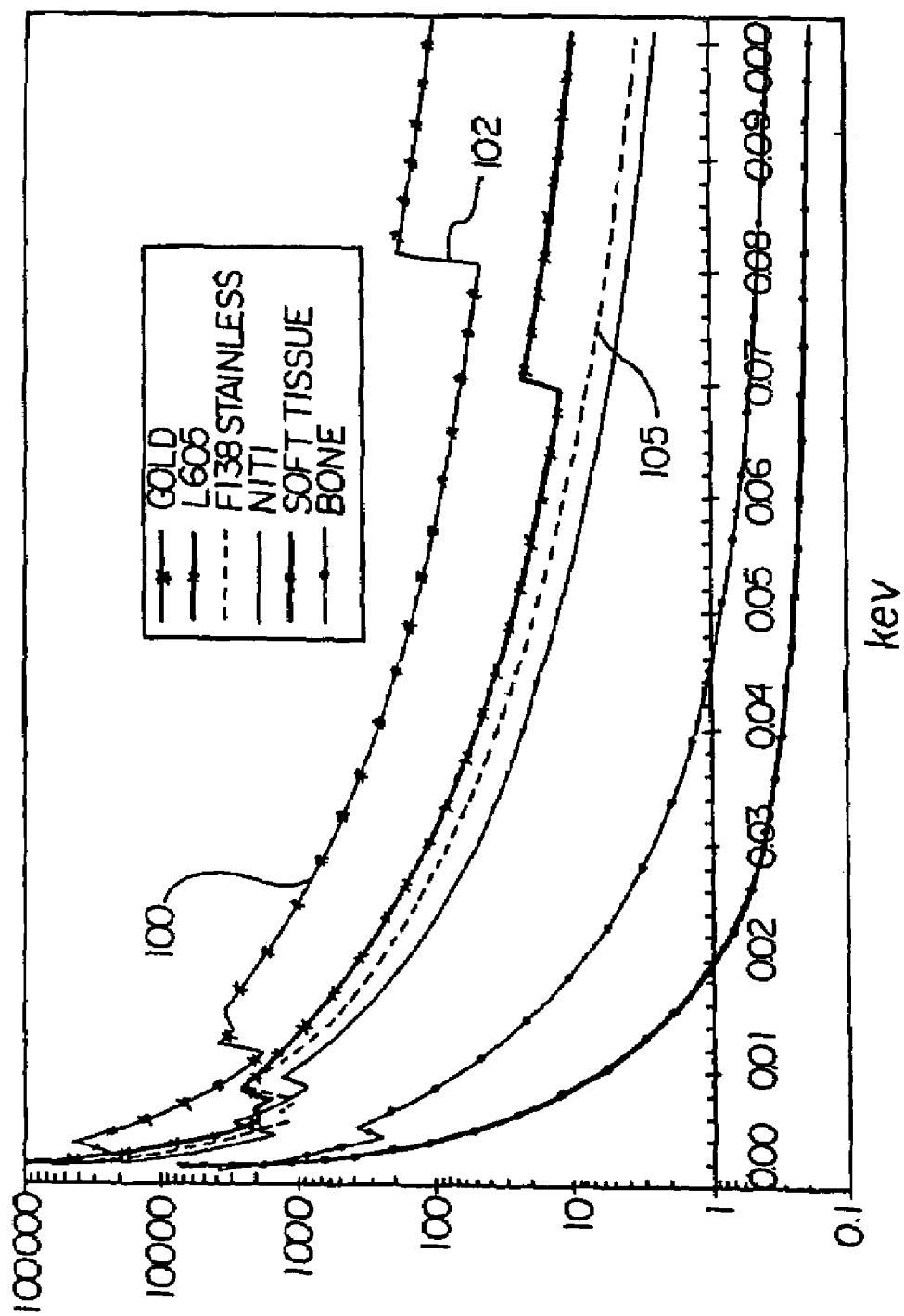
FIG. 1 is a graphical illustration of the attenuation of x-rays through various materials as a function of the energy of the x-rays. The attenuation coefficient is plotted on a logarithmic scale.

While this invention may be embodied in many different forms, there are described in detail herein specific preferred embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

Fluoroscopy is used for a variety of purposes including monitoring and aiding in the delivery and positioning of medical devices such as stents in desired bodily regions. To that end, medical devices in general and stents in particular are often provided with one or more radiopaque regions. Radiopaque regions of the medical device will absorb more energy than non-radiopaque regions of the medical device and hence, will appear as dark areas in a fluoroscopic image. Each material is characterized by its own attenuation curve. Attenuation curves of a number of different materials are shown in FIG. 1.

A number of different materials are typically used to provide a medical device with radiopacity. One such material is gold. As shown in FIG. 1, gold as illustrated by curve 100 has a higher attenuation coefficient than stainless steel, as shown in curve 105 and various tissues and hence will appear darker than stainless steel and various tissues in a radiographic image.

Certain materials that exhibit radiopacity are characterized by a discontinuity. As shown in attenuation curve 100 in FIG. 1, gold has a discontinuity 102 in its attenuation coefficient as a function of the incident energy of the photons directed at the gold. This discontinuity is referred to as a K-absorption edge. At the K-absorption edge, there is a precipitous change in the attenuation of radiation directed at the metal.

It has been found that this discontinuity may be exploited in a variety of imaging methods. This discontinuity has also been found useful in the design and manufacture of medical devices including stents.

In one embodiment, the invention is directed to a method of obtaining diagnostic information about a region of a living being, the region having a medical device including a radiopaque portion disposed therein. The radiopaque portion of the medical device is characterized by a K-absorption edge. In accordance with the method, an X-ray beam having a first energy level in excess of the K-absorption edge of the radiopaque portion of the medical device is applied to the region to obtain a first image information and radiographically locate the medical device within the living being. An X-ray beam having a second energy level at or below the K-absorption edge is applied to the region to obtain a second image information. Desirably, the step involving radiographically locating the medical device can precede the step of obtaining the second image information using an X-ray beam having a second energy level at or below the K-absorption edge.

Figure 2:
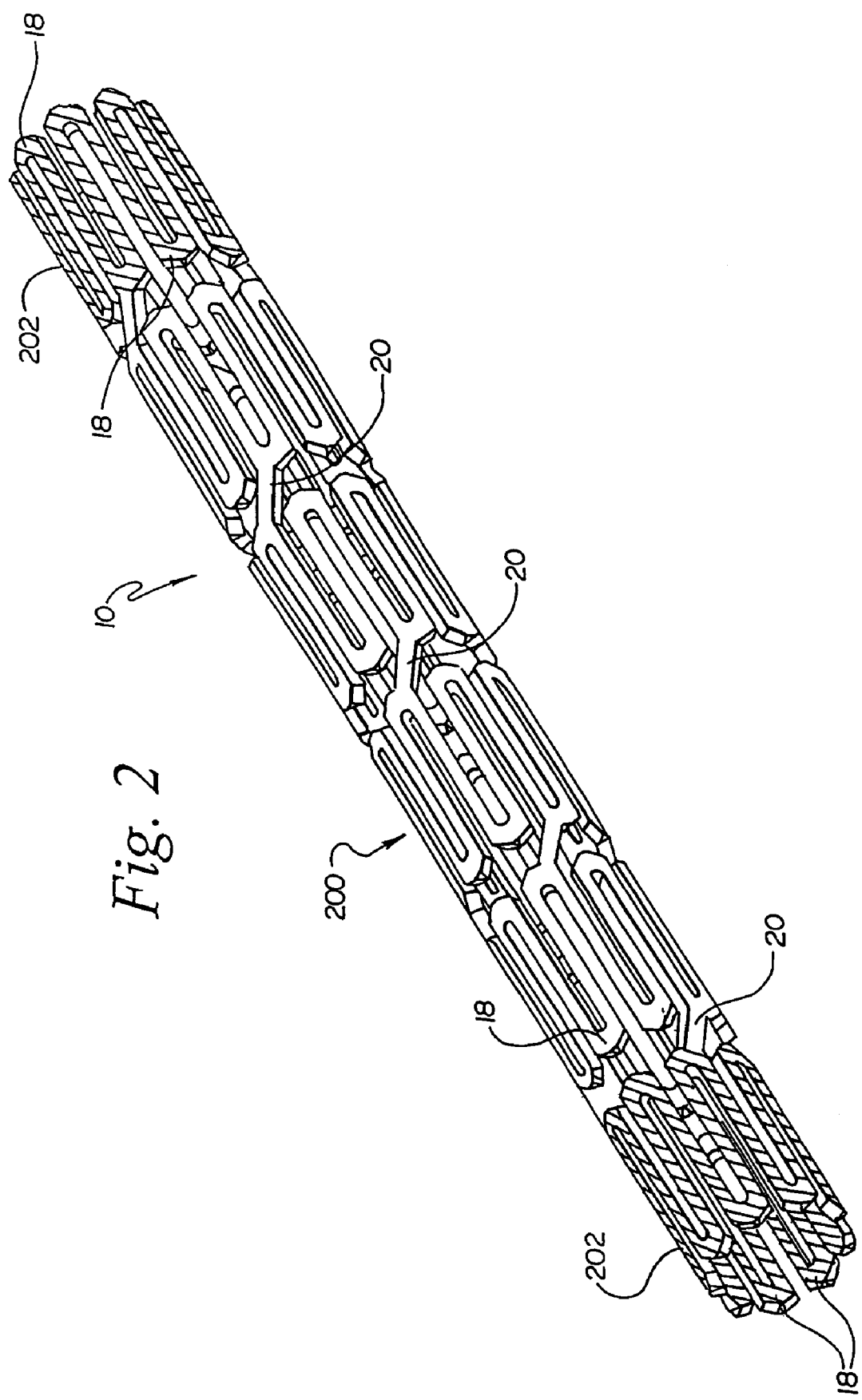
FIG. 2 is a side-elevational view of a stent having a radiopaque proximal end and a radiopaque distal end.
Figure 3:
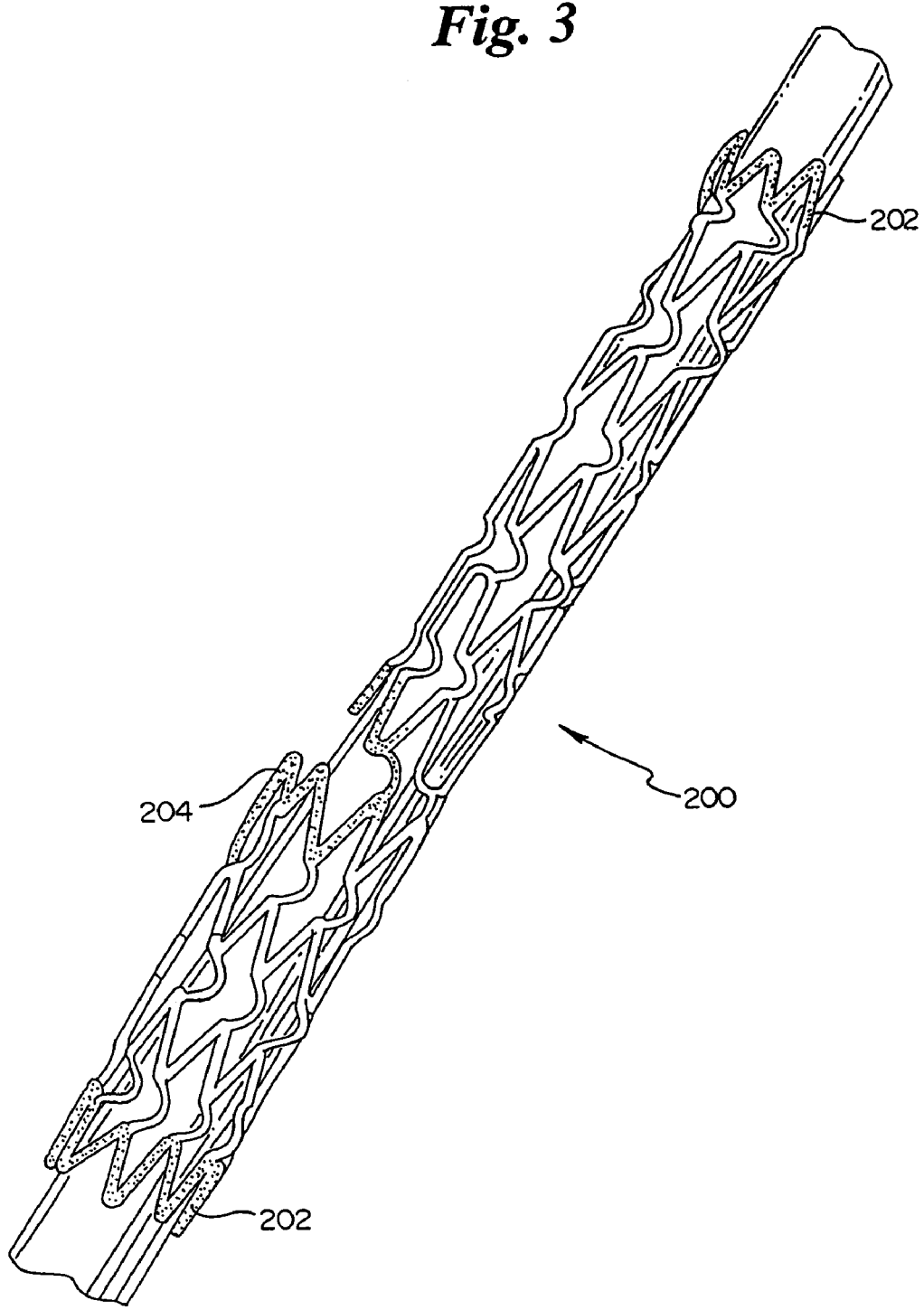
FIG. 3 is a side-elevational view of a stent having a radiopaque proximal end, a radiopaque distal end and a radiopaque region in a region of sidebranch access.

Desirably, the medical device is a stent. An example of a stent is shown at 200 in FIG. 2. Stent 200 may be self-expanding or balloon expandable. The entirety of the stent may be radiopaque or only certain portions of the stent may be radiopaque. For example, as shown in FIG. 2, one or both ends 202 of stent 200 are radiopaque, as indicated by the darkened regions of the stent. Another example of a stent is shown at 200 in FIG. 3. In addition to having optional radiopaque regions 202 at the proximal and distal ends of the stent, stent 200 of FIG. 3 has a region 204 of sidebranch access which is radiopaque. Adjacent regions can be non-radiopaque. Other suitable medical devices for use in the inventive methods include embolic agents and aneurysm fillers including liquid, gel, spherical and metallic coils, components of catheter tips, vena cava filters, and polymeric medical devices containing radiopaque elements with k-absorption shifts. An example of a vena cava filter is disclosed in U.S. Pat. No. 6,126,673. Embolic agents are disclosed in U.S. Pat. No. 5,637,086.

Any suitable, biocompatible radiopaque material may be used in the radiopaque portion of the medical device. Suitable radiopaque materials include but are not limited to one or more metals selected from the group consisting of gold, platinum and tantalum. The radiopaque material may also be an alloy comprising at least 10% tungsten by weight. An example of the latter is L-605. Other suitable materials for the radiopaque portion of the medical device or for the entirety or selected portions of the medical device include one or more inventive materials for stents such as titanium-tantalum alloys, tantalum-niobium alloys, and stainless steel alloys comprising at least one of platinum, gold, tantalum, and rhenium. Desirably, one or more of these materials are present in at least one of the first and second ends of the medical device.

The method may prove to be of particular value in obtaining information about the flow of a bodily fluid through a stent where the stent is located in a bodily vessel, the vessel having restenosed in the region of interest.

Desirably, in the practice of the inventive methods, the first and second energy levels are chosen such that the attenuation of the X-ray beam having the first energy level by the radiopaque portion is at least three times greater than the attenuation of the X-ray beam having the second energy level by the radiopaque portion.

As a non-limiting example of one of the inventive methods disclosed herein, a medical device such as a stent is delivered via catheter to a desired bodily location. The stent includes at least one radiopaque portion provided by a metal such as gold. Energy in excess of the K-absorption edge of the radiopaque portion of the stent is applied to the desired bodily location to obtain a first image information and radiographically locate the stent within the living being. An X-ray beam having a second energy level at or below the K-absorption edge of the metal is applied to the desired bodily location to obtain a second image information. The second energy level is chosen so that the radiopaque material does not obscure the contents of the stent. Thus, where the stent is implanted within a blood vessel and a contrast agent is included in the blood, the flow of blood through the radiopaque regions of the stent may be visualized, notwithstanding the presence of the radiopaque material, as a result of operating at an energy slightly below the K-absorption edge of the radiopaque metal. Desirably, energy at approximately 5 keV below the absorption edge is used.

In another embodiment, the invention is directed to a method of implanting a medical device which is expandable in a living body and monitoring flow through the medical device. The medical device may be any of those disclosed herein or any other suitable medical device. The method comprises the steps of delivering the medical device on a catheter to a desired location in a living body, locating the medical device by imaging the medical device with an X-ray beam having a first energy level in excess of the K-absorption edge of the radiopaque portion of the medical device, manipulating the catheter to expand the expandable medical device and visualizing flow of a bodily fluid comprising a contrast agent through the medical device by imaging the medical device with an X-ray beam having a second energy level at or below the K-absorption edge of the medical device.

Where the medical device is a balloon expandable stent, the manipulating step includes expanding a medical balloon disposed within the catheter to expand the stent. Where the stent is self-expandable, the manipulating step includes removing a restraining device, for example a sheath, from about the stent so that the stent is free to self-expand. It is noted that the term "stent" as used herein is intended to include within its scope stents, grafts and stent-grafts. Other suitable medical devices include, but are not limited to vena cava filters, embolic agents and aneurysm fillers including liquid, gel, spherical and metallic coils, components of catheter tips, and polymeric medical devices containing radiopaque elements with k-absorption shifts.

In yet another embodiment of the invention, the invention is directed to a method for radiographic imaging of a region of a body having a medical device with a radiopaque portion therein where the radiopaque portion has a K-absorption edge. The method comprises the steps of:

a) generating a plurality of X-ray beams with predetermined different energy spectra, at least one of the plurality of X-ray beams having a mean energy in excess of the K-absorption edge, at least one of the plurality of X-ray beams having a mean energy no greater than the K-absorption edge, b) illuminating the region with each of said plurality of beams; and c) acquiring a radiographic image of the region during illumination by each of said plurality of beams.

Desirably, the image acquired during the illumination step with the X-ray beam having a mean energy in excess of the K-absorption edge is used to locate the medical device, for example, a stent, and the image acquired during the illumination step with the X-ray beam having a mean energy at or below the K-absorption edge is used to visualize flow of a bodily fluid through the medical device.

The medical device may be any of the devices disclosed herein. Suitably, the medical device will be a stent.

The method may prove to be of particular value where the stent is in a bodily vessel and the vessel has restenosed in a region of the bodily vessel containing the stent.

Figure 4:
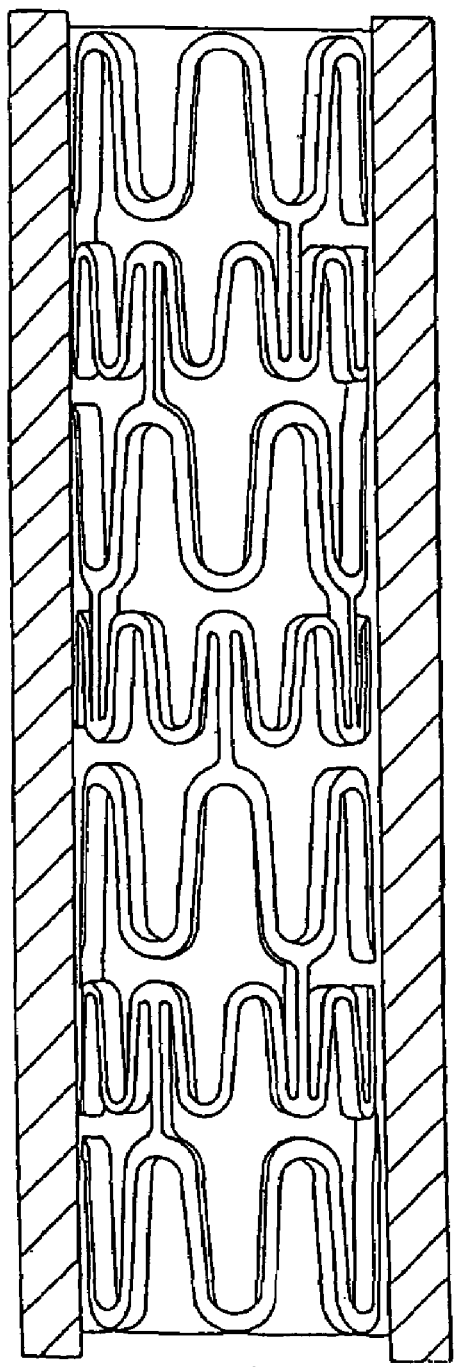
FIG. 4 is a schematic showing an X-ray image of a stent in a vessel when an X-ray beam having a mean energy in excess of the K-absorption edge energy of the radiopaque material is directed at the stent.
Figure 5:
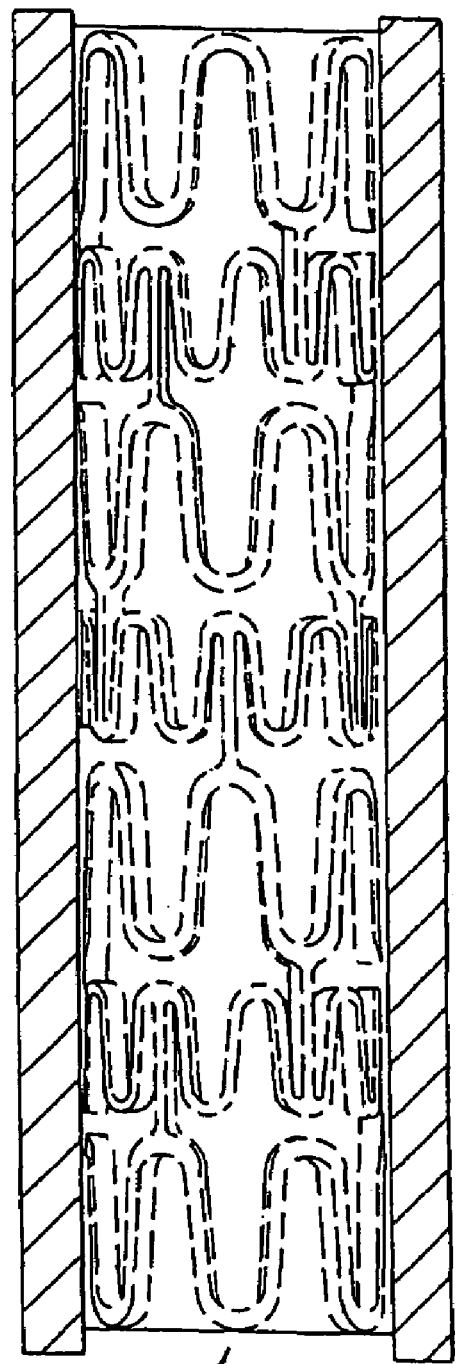
FIG. 5 is a schematic showing an X-ray image of a stent in a vessel when an X-ray beam having a mean energy in slightly less than the K-absorption edge energy of the radiopaque material is directed at the stent.

In yet another embodiment, the invention is directed to a stent having a flowpath therethrough, such as that shown at 200 in FIG. 2. At least a portion of stent 200 comprises an amount of a radiopaque material which is characterized by an attenuation curve having a K-absorption edge. As shown by way of example in FIG. 2, both ends 202 of the stent comprise a radiopaque material. The radiopaque material may be any of those disclosed herein or any other suitable radiopaque material. The amount of radiopaque material is chosen such that when an X-ray beam having a mean energy in excess of the K-absorption edge energy of the radiopaque material is directed at the stent and a radiographic image acquired, the radiopaque material is visible in the image and radiographically obscures any fluid in the flowpath of the stent. When an X-ray beam having a mean energy slightly below the K-absorption edge energy is directed at the stent, the radiopaque material is substantially transparent. Thus, the flow of a bodily fluid comprising a contrast agent such as iodinated nonionic contrast, ionic contrast or barium-based contrast may be visualized. In FIG. 4, a schematic is provided showing an X-ray image of stent 200 in vessel 302 when an X-ray beam having a mean energy in excess of the K-absorption edge energy of the radiopaque material is directed at the stent. Stent 200 appears dark in the image. FIG. 5 shows an X-ray image of the same stent 200 when an X-ray beam having a mean energy slightly below the K-absorption edge energy of the radiopaque material is directed at the stent. The surrounding blood which has a contrast agent is more readily visible in FIG. 5.

The invention is also directed to a method of designing a stent comprising the steps of selecting a stent structure, selecting a radiopaque material which is characterized by an attenuation curve having a K-absorption edge, selecting at least one portion of the stent structure which is to be provided with the radiopaque material and calculating an amount of the radiopaque material which must be provided in the selected portion of the stent structure such that the selected portion of the stent structure will be radiographically visible when an X-ray beam having a mean energy excess of the K-absorption edge energy is directed at the stent and such that the selected portion of the stent structure will be substantially radiographically transparent when an X-ray beam having a mean energy slightly below the K-absorption edge energy is directed at the stent.

The invention is further directed to a method of manufacturing a stent comprising the steps of selecting a stent structure, selecting a radiopaque material which is characterized by an attenuation curve having a K-absorption edge, selecting at least one portion of the stent structure which will be provided with the radiopaque material, calculating an amount of the radiopaque material which must be provided in the selected portion of the stent structure such that the selected portion of the stent structure will be radiographically visible when an X-ray beam having a mean energy excess of the K-absorption edge energy is directed at the stent and such that the selected portion of the stent structure will be substantially radiographically transparent when an X-ray beam having a mean energy slightly below the K-absorption edge energy is directed at the stent, and constructing a stent having the selected stent structure and comprising the selected radiopaque material in the selected portion of the stent, the radiopaque material present in the calculated amount.

The inventive methods disclosed herein may also be applied to designing and manufacturing other medical devices such as embolic agents and aneurysm filler including liquid, gel, spherical and metallic coils, components of catheter tips, vena cava filters, and polymeric medical devices containing radiopaque elements with k-absorption shifts.

The invention is also directed to a method of monitoring a treatment of a selected bodily region. The method comprises the steps of delivering a therapeutic agent to a desired bodily region, the therapeutic agent comprising a radiopaque material characterized by a K-absorption edge, generating a plurality of X-ray beams with predetermined different energy spectra, at least one of the plurality of X-ray beams having a mean energy in excess of the K-absorption edge, at least one of the plurality of X-ray beams having a mean energy no greater than the K-absorption edge, illuminating the region with each of said plurality of beams and, acquiring a radiographic image of the region during illumination by each of said plurality of beams. Desirably, the amount of the therapeutic agent present at the selected bodily region is calculated from the images. Using this technique, the location of the radiopaque treatment agent may be monitored by imaging the region with the radiopaque treatment agent at an energy slightly above the K-absorption edge and any other radiopaque substance in the region may then be imaged by reducing the energy to below that of the K-absorption edge of the radiopaque treatment agent.

Therapeutic agents having radiopaque materials include cisplatin and cisplatin derivatives, bis-platinum complexes and other platinum complexes. Examples of cisplatin derivatives are disclosed in U.S. Pat. No. 6,235,782. Examples of bis-platinum complexes are disclosed in U.S. Pat. No. 6,022,892.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

The particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction. In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the preferred and alternate embodiments of the invention. Those skilled in the art may recognize other equivalents to the specific embodiment described herein which equivalents are intended to be encompassed by the claims attached hereto.

What is claimed is:

1. A method of implanting a medical device which is expandable in a living body and monitoring flow through the medical device, the method comprising the steps of:
    delivering the medical device on a catheter to a desired location in a living body;
    locating the medical device by imaging the medical device with an X-ray beam having a first energy level in excess of the K-absorption edge of the radiopaque portion of the medical device;
    manipulating the catheter to expand the expandable medical device;
    visualizing flow of a bodily fluid comprising a contrast agent through the medical device by imaging the medical device with an X-ray beam having a second energy layer at or below the K-absorption edge of the medical device.

2. The method of claim 1, wherein the medical device is a stent.

3. The method of claim 1, wherein the stent is a balloon expandable and the manipulating step includes expanding a medical balloon disposed within the catheter.

4. The method of claim 2, wherein the stent is self-expandable and the manipulating step includes removing a restraining device from about the stent so that the stent is free to self-expand.

* * * * *

UNITED STATES PATENT AND TRADEMARK OFFICE
CERTIFICATE OF CORRECTION

PATENT NO. : 7,398,118 B2
APPLICATION NO. : 11/095429
DATED : July 8, 2008
INVENTOR(S) : David Knapp Page 1 of 1

It is certified that error appears in the above-identified patent and that said Letters Patent is hereby corrected as shown below:

Column 8, line 50 (Claim 1), please delete "layer" and insert --level-- therefor;

Column 8, line 54 (Claim 3), after "is" please delete "a".

Signed and Sealed this

Twenty-eighth Day of October, 2008

JON W. DUDAS
*Director of the United States Patent and Trademark Office*